United States Patent [19]

Omura et al.

[11] Patent Number: 4,537,940
[45] Date of Patent: Aug. 27, 1985

[54] ADHESIVE COMPOSITIONS

[75] Inventors: Ikuo Omura; Junichi Yamauchi, both of Kurashiki; Yoshinori Nagase, Takatsuki; Fumiko Uemura, Kurashiki, all of Japan

[73] Assignee: Kuraray Co., Ltd., Kurashiki, Japan

[21] Appl. No.: 659,455

[22] Filed: Oct. 10, 1984

Related U.S. Application Data

[63] Continuation of Ser. No. 570,292, Jan. 13, 1984, Pat. No. 4,499,251.

[30] Foreign Application Priority Data

Jan. 21, 1983 [JP] Japan .................................. 58-9170

[51] Int. Cl.³ .......................... C09K 3/00; C09J 3/14; C08F 30/02
[52] U.S. Cl. ................................ 526/278; 156/327; 156/331.2; 156/331.6; 523/115; 523/116; 524/547; 526/276; 526/277
[58] Field of Search .................. 526/278, 277, 276; 523/115, 116; 524/547; 156/327, 331.2, 331.6

[56] References Cited

U.S. PATENT DOCUMENTS

| | | | |
|---|---|---|---|
| 3,809,685 | 5/1974 | Sato et al. | 526/277 |
| 3,884,864 | 5/1975 | Matsuda et al. | 526/277 |
| 4,044,044 | 8/1977 | Saito | 526/278 |
| 4,222,780 | 9/1980 | Shibatani et al. | 106/35 |
| 4,259,117 | 3/1981 | Yamauchi et al. | 106/35 |
| 4,277,565 | 7/1981 | Oda et al. | 526/278 |
| 4,322,509 | 3/1982 | Zalucha | 526/278 |
| 4,442,239 | 4/1984 | Tsunekawa et al. | 523/116 |
| 4,443,197 | 4/1984 | Fusayama et al. | 433/228 |

FOREIGN PATENT DOCUMENTS

| | | |
|---|---|---|
| 1543758 | 4/1979 | United Kingdom . |
| 2089807 | 6/1982 | United Kingdom . |

*Primary Examiner*—Ronald W. Griffin
*Attorney, Agent, or Firm*—Oblon, Fisher, Spivak, McClelland & Maier

[57] ABSTRACT

This invention provides an adhesive composition which comprises 1 part by weight of (a) a compound of the general formula:

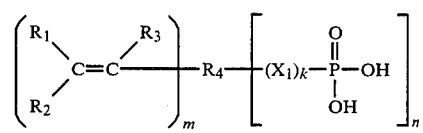

wherein $R_1$ represents H, a hydrocarbon group of 1–6 carbon atoms optionally containing halogen, COOR', wherein R' represents a hydrocarbon group of 1–20 carbon atoms optionally containing halogen or halogen;

$R_2$ is as defined for $R_1$;

$R_3$ represents H, a hydrocarbon group of 1–6 carbon atoms optionally containing halogen, halogen or CN;

$R_4$ represents $(COX_2)_{m1}(CO)_{m2}(ZCO)_{m3}(Z)_{m4}Ra$ wherein Ra represents an organic residue of 6–60 carbon atoms and a valency of $m+n$; m1, m2, m3 and m4 each represents an integer of 0–4 and satisfies $m1+m2+m3+m4 \leq m$; $X_2$ represents O, S or NRb, (wherein Rb represents H or alkyl of 1–4 carbon atoms and Z represents O or S;

$X_1$ is as defined for $X_2$;

m is an integer of 1–4;

n is an integer of 2–6; and k is 0 or 1, and 0–199 parts by weight of (b) a vinyl monomer copolymerizable with the aforesaid compound. Such an adhesive composition can strongly adhere to any of the hard tissues of the living body, such as teeth and bones, metal materials, organic polymer materials and ceramic materials, and, in particular, has an advantage in that it can maintain high adhesive strength for a long time under wet conditions. While the adhesive composition of this invention may be used in various fields, it is especially useful in the dentistry field.

12 Claims, No Drawings

ADHESIVE COMPOSITIONS

This is a continuation, of application Ser. No. 570,292, filed Jan. 13, 1984, now U.S. Pat. No. 4,499,251, issued Feb. 12, 1985.

BACKGROUND OF THE INVENTION

1. Field of the Invention

This invention relates to adhesive compositions which adhere strongly to any of the hard tissues of the living body, such as teeth and bones, metal materials, organic polymer materials and ceramic materials and are excellent in water resistance of adhesive strength. The term "adhesive compositions" as herein used not only means compositions used for bonding a plurality of adherends to one another, but also covers compositions used for forming highly adhesive coatings on the surfaces of adherends such as metal materials, organic polymer materials, etc. and compositions used for forming highly adhesive filling materials for repairing hard tissues of the living body. In other words, the adhesive compositions of this invention comprehend all the compositions which exhibit adhesion to and thus are applicable to various kinds of substances, such as hard tissues of the living body, metal materials, organic polymer materials, ceramic materials, etc.

2. Description of the Prior Art

Various kinds of metal materials, organic polymer materials and ceramic materials are used for the restoration of teeth. When these restorative materials are mounted in the mouth, it is necessary to ensure the adhesion between the teeth and the metal, organic polymer or ceramic material, and also the adhesion of the restorative materials to each other, for example, metal to metal, ceramics or organic polymer. In particular, since they are used in the mouth in the dentistry field, it is required that the adhesion be satisfactory under wet conditions.

Heretofore, a variety of attempts to use phosphate compounds in adhesive compositions have been made widely in the dentistry field.

(1) U.S. Pat. Nos. 4,259,075, 4,259,117 and 4,368,043 describe that a polymerizable composition containing a vinyl compound having a group of the formula:

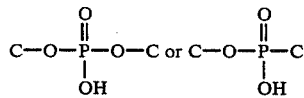

is effective as a dental adhesive. U.S. Pat. No. 4,222,780 describes that a polymerizable composition containing a vinyl compound having a group of the formula:

is also an effective dental adhesive. In fact, some of the compositions falling within the scopes of the above patents have been materialized and widely employed as primers for coating the cavity wall before the tooth cavity is filled. However, they had a problem in that the cavity wall must be acid etched beforehand in order to provide satisfactory adhesive strength to the tooth and also another problem in that they do not have satisfactory adhesive strength to a Ni - Cr alloy commonly employed in dentistry.

(2) Attempts to obtain adhesives having adhesion to tooth using polymerizable phosphate compounds have also been made and examples thereof include the following:

(i) U.S. Pat. No. 3,882,600 describes phosphoryl monofluoride.

(ii) Journal of Dental Research, vol. 53, p. 878–888 and vol. 56, p. 943–952, Chemical Abstract, vol. 77, p. 290 (66175 g) and Japanese Patent Application Laid-open No. 44152/1976 describe $CH_2=CH-PO(OH)_2$ and $CH_2=CHC_6H_4CH_2PO(OH)_2$.

(iii) Japanese Patent Application Laid-open No. 113843/1978 shows compounds, by a general formula, which are obtained by neutralizing one of the two hydroxyl groups in compounds of the formula:

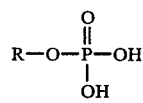

wherein R represents an organic residue having at least one vinyl group, and specific examples thereof include the following (wherein M represents an alkali metal): $CH_2=CHC_6H_4OPO(OH)(OM)$,

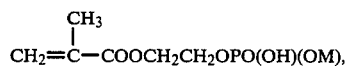

$CH_2=CHCH_2OPO(OH)(OM)$,

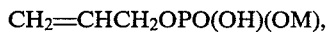

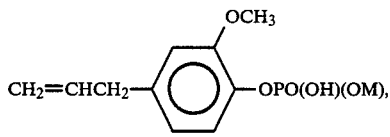

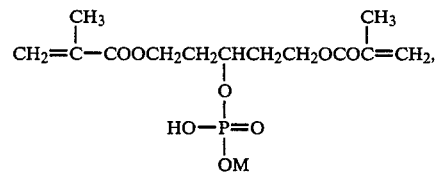

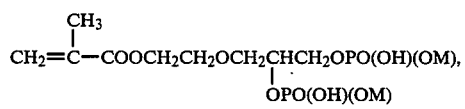

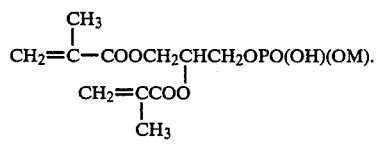

(iv) Japanese Patent Publication No. 49557/1982 describes methacryloyloxyethane-1,1-diphosphonic acid of the following formula:

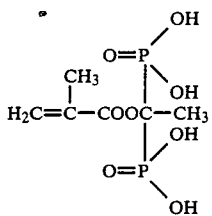

as an adhesive component in a dental adhesive.

In every case of the compounds described in (i) to (iv) above, high adhesive strength (especially to metals) under wet conditions cannot be obtained.

(3) Examples of other attempts to obtain adhesive compositions having adhesion to both teeth and metals include the following:

(i) U.S. Pat. No. 4,148,988 shows 4-methacryloxyethyl trimellitate as an adhesive monomer. This monomer, however, cannot maintain a strong bond between the tooth and a metal or organic polymer material for a prolonged time in the mouth which is under wet conditions and moreover under repeated occlusal pressure.

(ii) U.S. Pat. No. 3,872,047 and Japanese Patent Application Laid-open No. 98878/1974 disclose a polymer having both a hydrophilic group and a hydrophobic group as an adhesive component. As the monomer constituting said polymer, they disclose methacryloxyethyl phosphate, etc., but their adhesive strength seems inadequate.

(iii) It is known that a polymer obtained by polymerizing a vinyl monomer on the tooth surface by employing a ternary curing agent consisting of a peroxide, an amine and a sulfinic acid salt improves the adhesive strength to the tooth (U.S. Pat. No. 4,182,035). However, no satisfactory adhesive strength can be obtained by a combination with any conventional vinyl monomer, and thus it is necessary to explore a new adhesive vinyl monomer for this purpose.

(4) Further, attempts to employ phosphate compounds in adhesive compositions have been made widely in various industries. Examples thereof are disclosed in U.S. Pat. Nos. 3,754,972, 3,884,864, 3,987,127, 4,001,150, 4,044,044, 4,223,115; Japanese Patent Application Laid-open Nos. 20238/1974, 100596/1975, 125182/1976, 12995/1978, 11920/1981, 44638/1982; Japanese Patent Publication Nos. 4126/1980, 4790/1980, etc. However, none of these phosphate compounds described in the above patent literature are free from a problem associated with water resistance of adhesive strength.

SUMMARY OF THE INVENTION

It is an object of this invention to provide an adhesive composition which adheres excellently and hence is used for bonding (a) a hard tissue of the vital body and (b) a hard tissue of the vital body or a material for restoring said tissue (for example, a metal material, an organic polymer material, a ceramic material, etc.) or used for filling and restoring a hard tissue of the vital body.

It is another object of this invention to provide an adhesive composition for industrial and domestic use for bonding (a) a metal material and (b) a metal material, an organic polymer material or a ceramic material or bonding a ceramic material and a ceramic material or an organic polymer material, or an adhesive composition used in coating agents, paints, etc. for forming a coating having excellent adhesion on the surface of a metal material or a ceramic material.

It is still another object of this invention to provide a dental adhesive composition for coating the cavity surface of a tooth before the tooth is filled and restored thereby forming a strong bond between the tooth and a filling material.

It is a further object of this invention to provide a dental filling composition having excellent adhesion to teeth and hence used for filling and restoring tooth cavities.

It is yet another object of this invention to provide a dental adhesive composition for bonding and fixing a tooth and a dental restorative material (e.g. inlay, onlay, abutment tooth, bridge, post, splint, orthodontic bracket, crown etc.) or dental restorative materials to each other (e.g. abutment tooth and crown).

Further, an additional object of this invention is to provide a dental adhesive composition used as a pit and fissure sealant for coating the tooth surface for preventing caries.

Still an additional object of this invention is to provide a method for treating teeth which comprises making the restoration of a tooth even further complete by stably and strongly bonding the tooth and a restorative material, or restorative materials to each other, or which comprises preventing dental caries by coating the tooth surface.

The above objects of this invention may be attained by an adhesive composition which comprises 1 part by weight of (a) a compound of the general formula:

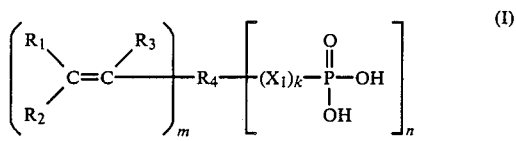

wherein $R_1$ represents H, a hydrocarbon group of 1-6 carbon atoms optionally containing halogen(F, Br, Cl or I), COOR', wherein R' represents a hydrocarbon group of 1-20 carbon atoms optionally containing halogen or halogen;

$R_2$ is as defined for $R_1$;

$R_3$ represents H, a hydrocarbon group of 1-6 carbon atoms optionally containing halogen, halogen or CN;

$R_4$ represents $(COX_2)_{m1}(CO)_{m2}(ZCO)_{m3}(Z)_{m4}Ra$ wherein Ra represents an organic residue of 6-60 carbon atoms and a valency of m+n; m1, m2, m3 and m4 each represents an integer of 0-4 and satisfies $m1+m2+m3+m4 \leq m$; $X_2$ represents O, S or NRb, wherein Rb represents H or alkyl of 1-4 carbon atoms and Z represents O or S [for example, where m=2, m1=1 and m2=1, this formula indicates that Ra is connected to the two unsaturated carbon atoms via $COX_2$ and CO respectively];

$X_1$ is as defined for $X_2$, m represents an integer of 1-4, n is an integer of 2-6, and k is 0 or 1, with the proviso that where m is 2 or more, the plurality of each of $R_1$, $R_2$ and $R_3$ may be the same or different and where a plurality of $X_1$ and/or $X_2$ are present, they may be the same or different, and 0-199 parts by weight of (b) a vinyl monomer.

DETAILED DESCRIPTION OF THE PREFERRED EMBODIMENTS

The adhesive compositions of this invention are characterized in that the above compound (I) is used as a monomer imparting adhesion to hard tissues of the vital body, metals and ceramics (which is hereinafter sometimes referred to as the "adhesive monomer"). [For reference, adhesive compositions containing a compound of the formula (I) above wherein n is 1 as a constituting element are covered by our earlier patent applications (U.S. patent application Ser. No. 398,437, now abandoned, and European Patent Application No. 82303942.5)].

By the term "organic residue" as herein used is meant to cover the following (i) and (ii):

(i) a hydrocarbon group optionally containing OH, COOH, $NH_2$ or halogen as a substituent; and (ii) a group composed of a plurality of (2–20) hydrocarbon groups of the type defined in (i) above, said hydrocarbon groups being connected to one another by linkages selected from ether type, thioether type, ester type, thioester type, thiocarbonyl type, amide type, carbonyl type, sulfonyl type, urethane type, -NH- type,

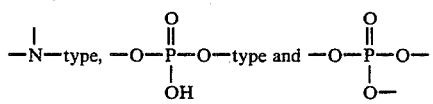

type linkages. In this case, not only those in which the backbone of the organic groups is composed of the hydrocarbon groups but also those in which a part of the hydrocarbon groups constitutes the side-chain of the organic residue backbone are included in this definition.

Applicable such organic residues are illustrated by the following formulae, in which A represents a hydrocarbon group, and B represents a linkage selected from —O—,

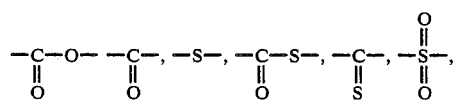

—CONH—, —OCONH—, —NH—,

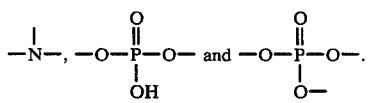

For the sake of simplicity, the double bond side is represented by [C=C], and the phosphoric or phosphonic acid side is represented by [$PO_3H_2$].

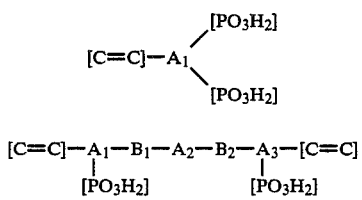

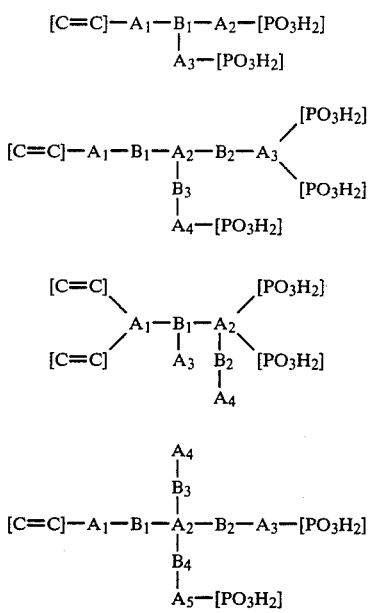

The term "hydrocarbon group" in this invention is used herein in a broad sense to also cover a halogenated hydrocarbon group unless otherwise specified.

Of the compounds of the formula (I), vinyl compounds wherein $R_1$ and $R_2$ are both hydrogen, $R_3$ is hydrogen or methyl and $R_4$ is $(COX_2)_m Ra$, i.e. compounds of the formula:

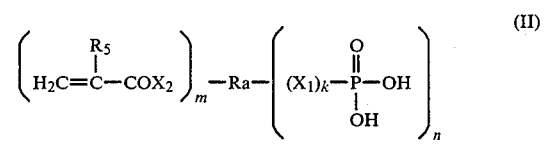

wherein $R_5$ represents hydrogen or methyl are particularly preferred.

In the formula (II), it is preferred that said Ra is either (a) a hydrocarbon group of 6–60 carbon atoms optionally substituted by halogen, hydroxyl, amino or carboxyl or (b) a group of 6–60 carbon atoms composed of 2–15 hydrocarbon groups, each hydrocarbon group being of 1–59 carbon atoms and at least one thereof being of at least 3 carbon atoms, which hydrocarbon groups are connected to one another by the aforesaid various linkages. Of the compounds of the formula (II), those wherein n is 2 and which are illustrated below are particularly practical compounds because the synthesis is relatively easy.

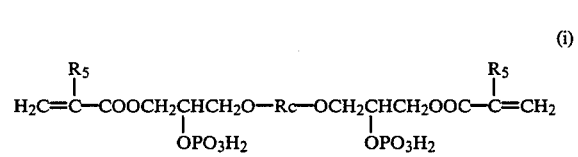

wherein $R_5$ is hydrogen or methyl, and Rc is a divalent organic residue of 2–54 carbon atoms;

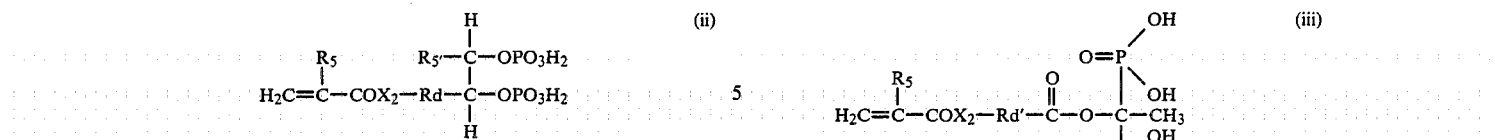
wherein $R_5$ and $R_{5'}$ each is hydrogen or methyl, $X_2$ is O, S or NRb and Rb is a divalent organic residue of 4–57 carbon atoms; and
wherein $R_5$, and $X_2$ are as defined above, and $R'_d$ is a divalent organic residue of 3–57 carbon atoms.
Specific examples of the adhesive monomers having a plurality of —$PO_3H_2$ groups used in this invention are given below:
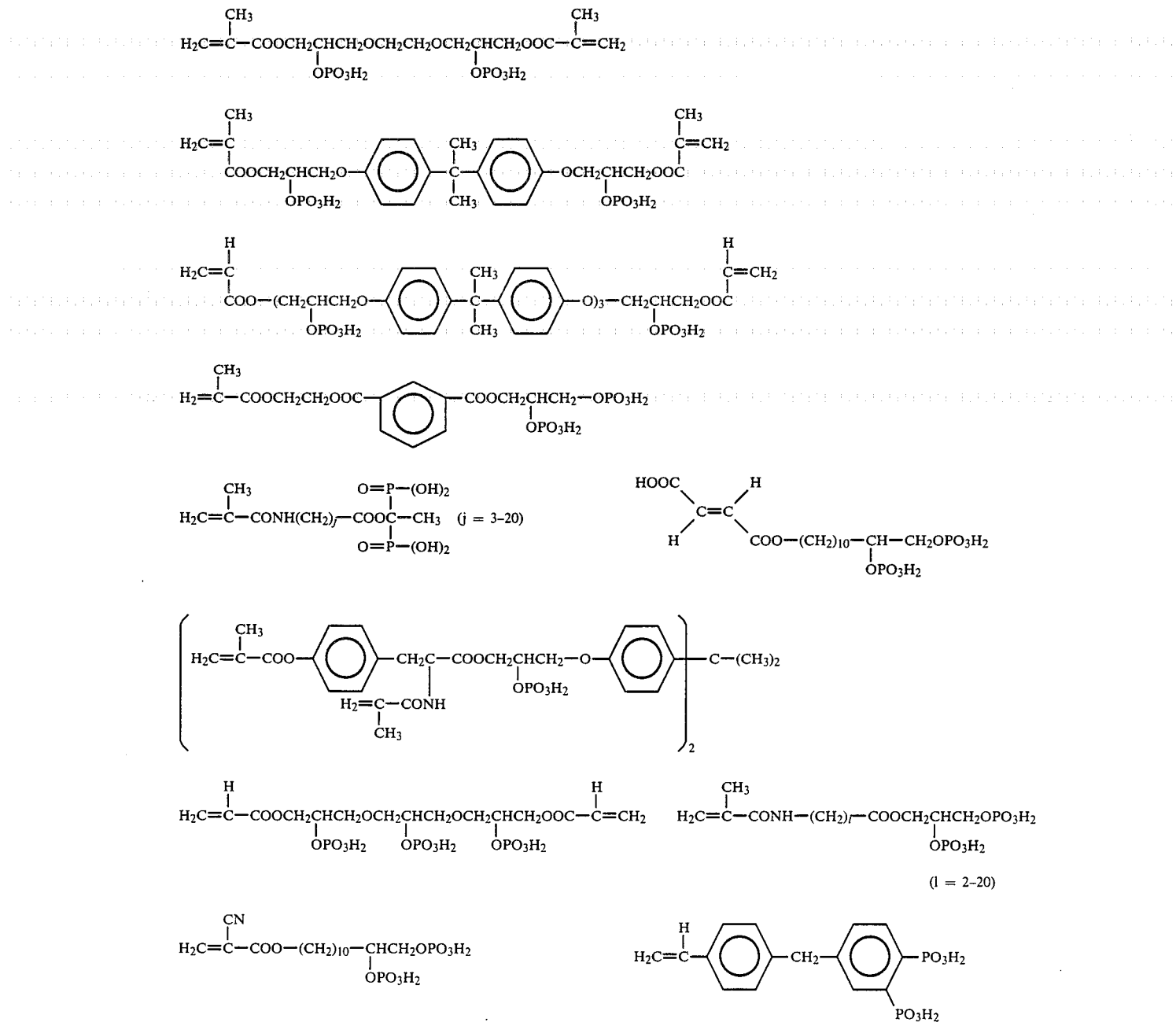

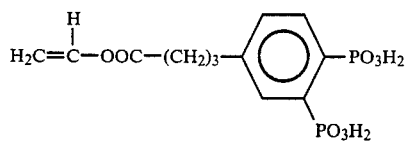
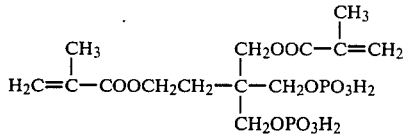
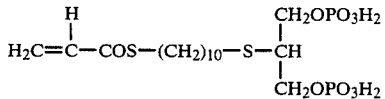
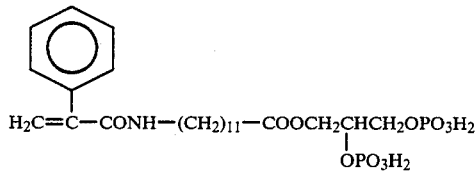
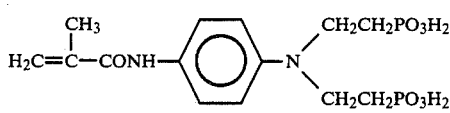
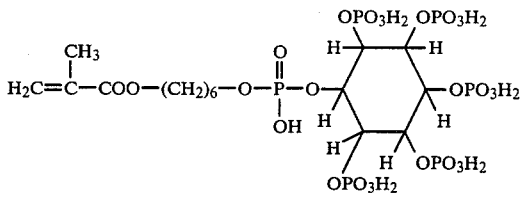
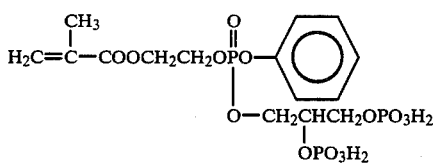
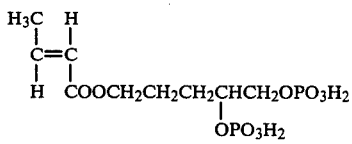
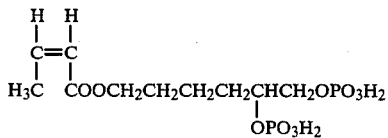
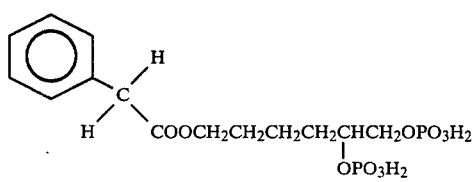
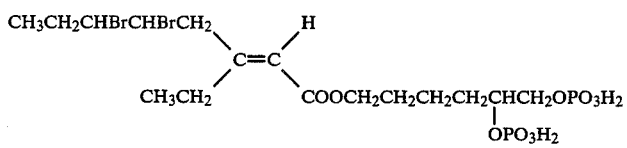
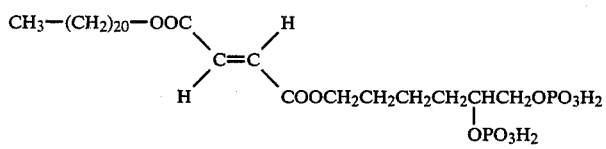
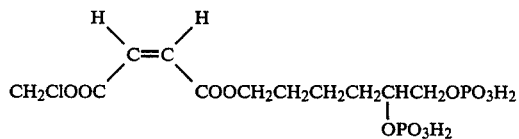
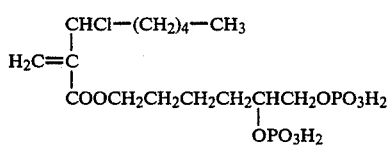
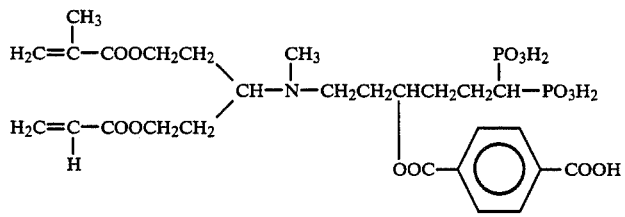

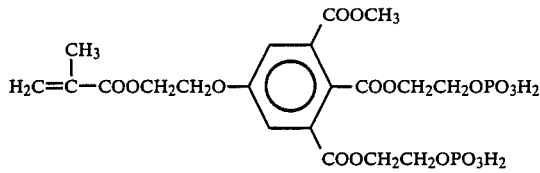
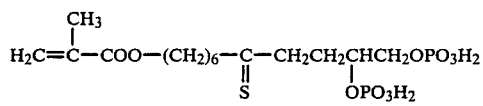
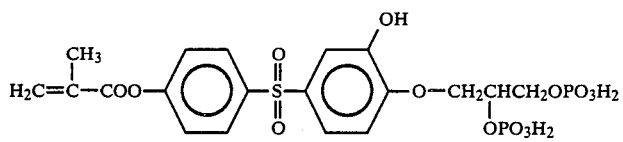
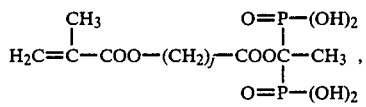
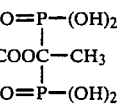

(j = 3-20)

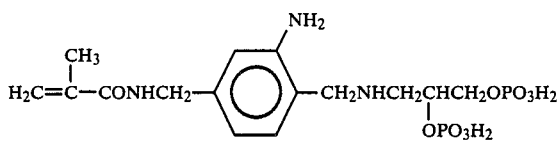
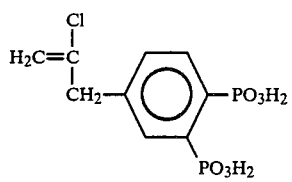

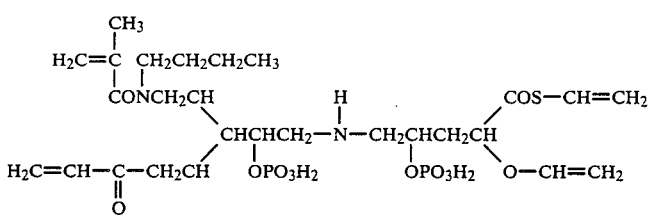

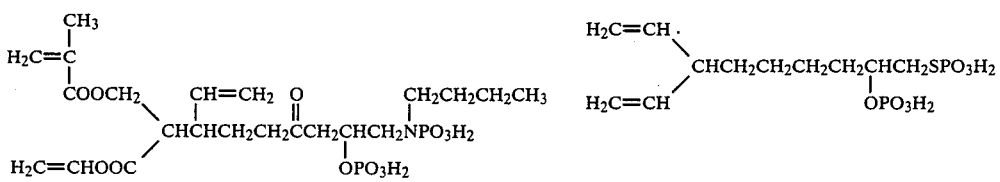

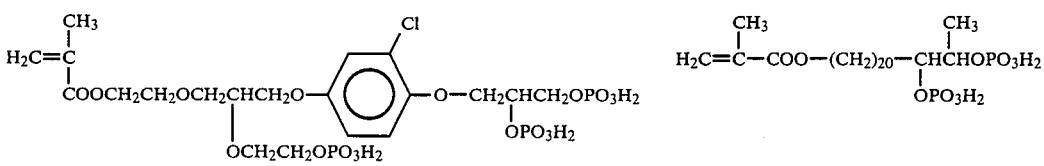

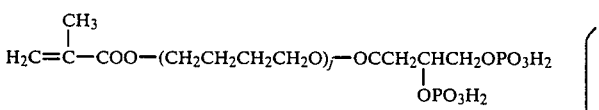

(j = 1-14)

In the compounds of the formula (I), if Ra is of 4 or less carbon atoms, the adhesive strength to teeth and metal and the like materials and its water resistance are extremely poor as compared with the compounds used in this invention. In general, there is a tendency that the adhesive strength becomes higher with the increase in number of the carbon atoms in Ra, and the highest adhesive strength is exhibited in the range of 8-40 carbon atoms. However, when the number of the carbon atoms increases and exceeds 50, the adhesive strength begins to decrease. Therefore, in order to achieve the objects of this invention, it is necessary that the upper limit for the carbon atoms in Ra be not greater than 60.

In the adhesive composition of this invention (which is hereinafter sometimes referred to as the "adhesive composition"), the compound of the formula (I) is used in combination with a vinyl monomer copolymerizable with said compound. By the selection of the copolymerizable vinyl monomer, the viscosity, wettability, curability, mechanical properties etc. of the adhesive may be controlled. While the vinyl monomer is appropriately selected according to the intended purpose and use, it is general to use a (meth)acrylate type monomer, a styrene type monomer or vinyl acetate. In addition to the above, acrylamides such as (meth)acrylamide, N-n-butoxymethyl(meth)acrylamide, N-(hydroxymethyl)acrylamide, etc., (meth)acrylic acid, isobutyl vinyl ether, diethyl fumarate, diethyl maleate, maleic anhydride, methyl vinyl ketone, allyl chloride, vinylnaphthalene, vinylpyridine, etc. are also used. Examples of the above-described styrene type monomer include compounds of the formula:

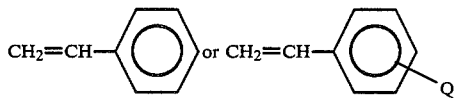

wherein Q is halogen or a hydrocarbon group of 1-6 carbon atoms, e.g., divinylbenzene, p-chlorostyrene, etc. As the (meth)acrylate type monomer, compounds generally often used in anaerobic adhesives, dental adhesives, etc. may also be favorably used in this invention. As the (meth)acrylate type monomer, a (meth)acrylate type monomer of the formula:

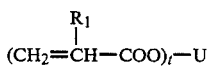

wherein $R_1$ represents H or $CH_3$, U represents an organic group of 1-50 carbon atoms, and t represents an integer of 1-4 (for the definition of the organic group, refer to the description hereinabove) is used. Examples of such a monomer include the following:

(i) Monofunctional (meth)acrylates:

Methyl (meth)acrylate, ethyl (meth)acrylate, n-butyl (meth)acrylate, isobutyl (meth)acrylate, n-hexyl (meth)acrylate, 2-ethylhexyl (meth)acrylate, benzyl (meth)acrylate, decyl (meth)acrylate, lauryl (meth)acrylate, stearyl (meth)acrylate, 2-hydroxyethyl (meth)acrylate (sometimes referred to as HEMA), 2-hydroxypropyl (meth)acrylate, dimethylaminoethyl (meth)acrylate, diethylaminoethyl (meth)acrylate, 3-chloro-2-hydroxypropyl (meth)acylate, 2,3-dibromopropyl (meth)acrylate, etc.

(ii) Difunctional (meth)acrylates:

(a) Those wherein U is $-CH_2CH_2(OCH_2CH_2)_s-$ or

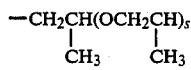

wherein s is an integer of 0-15:

Ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, etc.

(b) Those wherein U is alkylene (generally of 3-12 carbon atoms):

Propanediol di(meth)acrylate, glycerin di(meth)acrylate, 1,3-butanediol di(meth)acrylate, 1,4-butanediol di(meth)acrylate, 1,5-pentanediol di(meth)acrylate, 1,6-hexanediol di(meth)acrylate, neopentylglycol di(meth)acrylate, 1,10-decanediol di(meth)acrylate, 2,3-dibromoneopentylglycol di(meth)acrylate, etc.

(c) Those wherein U has a residue of a bisphenol A derivative:

Bisphenol A di(meth)acrylate, 2,2-bis[(meth)acryloyloxypolyethoxyphenyl]propane, i.e.

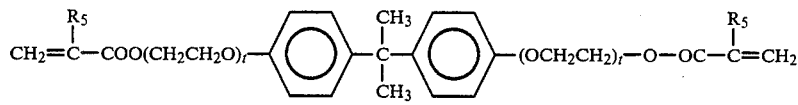

wherein t is an integer of 1-9, 2,2'-bis(4-acryloyloxypropoxyphenyl)propane, 2,2-bis[4-(3-methacryloyloxy-2-hydroxypropoxy)phenyl]propane (sometimes referred to as Bis-GMA), etc. Among the above, those wherein U is of 15-30 carbon atoms are favorably employed.

(d) Those wherein U is

wherein u is 1 or 2:

1,2-Bis[3-(meth)acryloyloxy-2-hydroxypropoxy]ethane, 1,4-bis[3-(meth)acryloyloxy-2-hydroxypropoxy]butane etc.

(e) Urethane di(meth)acrylates wherein U is JOCONHTNHCOOJ wherein J is alkylene (generally of 2-10 carbon atoms), and T is an organic diisocyanate residue of 1-50 carbon atoms:

For example, those described in Japanese Patent Application Laid-open No. 687/1975 are employed.

(iii) Tri- and tetrafunctional methacrylates:

Trimethylolpropane tri(meth)acrylate, trimethylolethane tri(meth)acrylate, tetramethylmethane tri(meth)acrylate, tetramethylolmethane tetra(meth)acrylate, N,N'-(2,2,4-trimethylhexamethylene) bis[2-(aminocarboxy)propane-1,3-diol] tetramethacrylate, etc.

These copolymerizable monomers are used either singly or in a combination of several thereof. Of these monomers, that preferred for use in dental adhesives is a methacrylate, and it is desired that it constitute 50% by weight or more of the copolymerizable monomer. Preferred examples of the methacrylate include methyl methacrylate, ethyl methacrylate, HEMA, n-hexyl methacrylate, benzyl methacrylate, lauryl methacrylate, Bis-GMA, bisphenol A dimethacrylate, 2,2-bis[(meth)acryloyloxypolyethoxyphenyl]propane, ethylene glycol dimethacrylate, diethylene glycol dimethacrylate, triethylene glycol dimethacrylate 1,6-hexanediol dimethacrylate, 1,10-decanediol dimethacrylate, neopentyl glycol dimethacrylate, trimethylolethane trimethacrylate, etc.

In the adhesive composition of this invention, it is necessary to use the compound of the formula (I) in an amount of 0.5% by weight or more, that is, to use 0-199 parts by weight of the aforesaid copolymerizable monomer per part by weight of the compound of the formula (I). With the amount of less than 0.5% by weight, the adhesive strength is inadequate. It is more preferred to use the compound of the formula (I) in an amount of 1.5% by weight or more.

The adhesive composition of this invention is applied to a surface to be bonded, and polymerized and cured either by physical means such as heating, or irradiation with X-rays or ultraviolet light or visible light, or by chemical means, e.g. using a polymerization initiator, to exhibit a bonding function. Although a certain type of the compounds (I) of this invention, that is, that wherein $R_3$ is CN can provide a composition curable without using a curing agent, it is general to effect curing by irradiating with light in the presence of a photosensitizer or adding a polymerization initiator. In this invention, the term "curing agent" is used to include both polymerization initiator and photosensitizer. Examples of the usable curing agent are varied; for example: organic peroxides, azo compounds, organic metal compounds, redox type initiators, photosensitizers, for ultraviolet or visible light, etc. Specific examples thereof include benzoyl peroxide, di-t-butyl peroxide, cumene hydroperoxide, t-butyl hydroperoxide, methyl ethyl ketone peroxide, azobisisobutyronitrile, tributylborane, organic sulfinic acids or salts thereof, hydrogen peroxide/$Fe^{2+}$ salt systems, cumene hydroperoxide/$Fe^{2+}$ salt systems, benzoyl peroxide/N,N-dialkylaniline derivative systems, ascorbic acid/$Cu^{2+}$ salt systems, organic sulfinic acid (or salt thereof)/amine (or salt thereof)/peroxide systems, $\alpha$-diketone/allylthiourea systems (visible light type), benzoin methyl ether, benzoin ethyl ether, benzil, diacetyl, diphenyl disulfide, di-$\beta$-naphthyl sulfide, etc. Of the above, those preferred for use in dental adhesive compositions are benzoyl peroxide, azobisisobutyronitrile, tributylborane, organic sulfinic acids or salts thereof, and aromatic sulfinc acid (or salt thereof)/diacyl peroxide/aromatic secondary or tertiary amine (or salt thereof) systems. Examples of the aromatic sulfinic acids include benzenesulfinic acid, p-toluenesulfinic acid, $\beta$-naphthalenesulfinic acid, styrenesulfinic acid, etc. The cation for forming a salt with said sulfinic acid can be, for example, an alkali metal ion, an alkaline earth metal ion, an ammonium ion, etc., of which the alkali metal ion and the alkaline earth metal ion are superior in terms of storage stability and adhesive strength. Examples thereof include $Li^+$, $Na^+$, $K^+$, $Mg^{2+}$, $Ca^{2+}$, $Sr^{2+}$, etc. Preferred specific examples of the aromatic amines include N,N-dimethylaniline, N,N-dimethyl-p-toluidine, N,N-diethanolaniline, N,N-diethanol-p-toluidine, N-methylaniline, N-methyl-p-toluidine, etc. These amines may also form salts with hydrochloric acid, acetic acid, phosphoric acid, etc. Examples of the diacryl peroxides include benzoyl peroxide, m-toluoyl peroxide, 2,4-dichlorobenzoyl peroxide, octanoyl peroxide, lauroyl peroxide, succinic acid peroxide, etc., of which benzoyl peroxide and m-toluoyl peroxide are particularly preferred. The curing agent is employed in an amount of 0.01-20 parts by weight per 100 parts by weight of the polymerizable monomer employed, especially preferably in the range of 0.1-15 parts by weight.

It is sometimes desired to add a volatile organic solvent having a boiling point of 150° C. or below at 760 Torr to the adhesive composition of this invention. Such an embodiment is preferred in the case where the adhesive composition of this invention is employed as a primer used in filling a dental filling material in a tooth cavity. The volatile organic solvent thus applied is evaporated by blowing air or nitrogen, thereby a coating of the vinyl compound is formed on the adherend surface. Examples of the orqanic solvent suitable for such a using method include methanol, ethanol, acetone, methyl ethyl ketone, methyl acetate, ethyl acetate, dichloromethane, chloroform, diethyl ether, diisopropyl ether, toluene, etc. The proportion of such a volatile solvent to the total polymerizable monomers is 300 times (by weight) or less, preferably 100 times or less. A large dilution exceeding 300 times exhibits a great reduction in the adhesive strength probably because the coating of the polymerizable monomer formed on the adherend surface is too thin.

The adhesive composition of this invention may sometimes contain a conventionally known filler of an inorganic or organic polymer or an inorganic - organic composite type. By adding the filler, the adhesive composition of this invention may be used as a dental cement for adhesion and filling, a dental composite resin and a bone cement. The amount of the filler added is up to 1000 parts by weight, preferably 20–500 parts by weight, per 100 parts by weight of the polymerizable monomer. By the addition of the filler, the rheological properties of the adhesive composition on use and the mechanical properties, adhesive strength and water resistance of the cured composition are improved. Examples of the inorganic filler used in this invention include natural minerals such as quartz, felstone, pottery stone, wallastonite, mica, clay, kaolin, marble, etc., ceramics such as silica, alumina, silicon nitride, boron carbide, boron nitride, glass, e.g., soda glass, barium glass, strontium glass and borosilicate glass, glass-ceramics containing lanthanum, etc., and water-insoluble salts such as barium sulfate, calcium carbonate, etc. The inorganic filler is generally surface-treated with a silane coupling agent, such as $\gamma$-methacryloyloxypropyltrimethoxysilane, vinyltrimethoxysilane, vinyltriethoxysilane, vinyltrichlorosilane, vinyltris(2-methoxyethoxy)silane, vinyltriacetoxysilane, $\gamma$-mercaptopropyltrimethoxysilane, etc. Examples of the organic polymer filler include various polymers such as polymethyl methacrylate, polyamides, polyesters, polypeptides, polysulfones, polycarbonates, polystyrene, chloroprene rubber, nitrile rubber, styrene butadiene rubber, polyvinyl acetate, etc. Examples of the inorganic - organic composite type filler include those obtained by coating the above-described silane-treated inorganic fillers with the above-described various polymers.

These fillers may be used either singly or in a combination of several thereof. The particle size of the filler is usually not greater than 100 u, and the shape may be either formless, spherical, lamellar or fibrous. If a polymer is used, it may also be dissolved in a polymerizable monomer or a volatile organic solvent. Where the adhesive composition of this invention is used as a dental cement or a dental composite resin, the filler is preferably an inorganic filler or an inorganic - organic composite type filler.

Further, the adhesive composition of this invention, in particular, the adhesive composition for industrial and domestic use, may be modified by dissolving an organic solvent soluble polymer such as PMMA, polystyrene, polyvinyl acetate, chloroprene rubber, butadiene rubber, nitrile rubber, chlorosulfonated polyethylene, etc. in an amount of up to 200 parts by weight, preferably up to 120 parts by weight, per 100 parts by weight of the vinyl monomer composition used in this invention, to aid the thickening of said adhesive composition, the improvement of the mechanical properties of the cured composition, etc.

In addition to the above-described various components, the adhesive composition of this invention may further contain, for example, a polymerization inhibitor such as hydroquinone monomethyl ether (MEHQ), an antioxidant such as 2,6-di-tertbutyl-p-cresol (BHT), an ultraviolet absorbing agent, various pigments and dyes, a phthalic acid diester, silicone oil, etc., if necessary, depending on the required performance as a practical adhesive composition. These are added as small amount additives in amounts of up to 10 parts by weight, generally up to 5 parts by weight, per 100 parts by weight of the polymerizable monomers.

When the adhesive composition of this invention is used for dental, orthopedic or other medical purposes, a room temperature curing redox type initiator may often be used. In such a case, it is necessary to ensure the storage stability of the composition and hence to choose an appropriate package form which can keep the oxidant and the reducing agent apart from each other. Examples of the package form include two-part packages of (a) the vinyl compound plus the reducing agent in one and (b) the vinyl compound plus the oxidant in the other, two-part packages of (a) the vinyl compound plus the oxidant (or reducing agent) and (b) the volatile organic solvent plus the reducing agent (or oxidant), two-part packages of (a) the vinyl compound plus the oxidant (or reducing agent) and (b) the filler plus the reducing agent (or oxidant), two-part packages of (a) the vinyl compound, the filler plus the oxidant and (b) the vinyl compound plus the filler plus the reducing agent, etc. In an organic sulfinic acid (or salt thereof)/amine (or salt thereof)/peroxide ternary system, which is particularly suitable, among the redox type polymerization initiators, for the adhesive composition of this invention, the sulfinic acid and the amine are the reducing agent and the peroxide is the oxidant. In this case, it is also possible to choose a three-part package form in which the sulfinic acid and the amine are packed separately.

Where a photosensitizer is employed as the curing agent, the vinyl compound plus the photosensitizer must be stored in a container shielded against light. Where an initiator which initiates polymerization in a short time once it is brought into contact with a vinyl compound (e.g. tributylborane, etc.), it is necessary to pack the vinyl compound and the polymerization initiator separately. The thus separately packed adhesive composition is mixed together just before use.

The adhesive composition of this invention adheres excellently to any of the following materials, and maintains high adhesive strength for a long time even under wet conditions:

(1) hard tissues of the living body, such as teeth and bones;
(2) metal materials, including not only non-precious metals such as iron, nickel, chromium, aluminum, cobalt, copper, zinc and tin, or stainless steel, brass or other alloys thereof, but also precious metal alloys containing 50–90% of gold or platinum, which have hitherto been difficult to bond with any conventional adhesive;
(3) ceramics, such as glass, porcelain, silica and alumina; and
(4) organic polymer materials, such as polymethyl methacrylate, polyesters, polyamides, polyurethanes, polycarbonates, polysulfones, polystyrene, etc.

The adhesive composition of this invention may be used in various application fields because of its excellent adhesion to various materials as described above. Preferred examples of its applications are given below:

(i) Dental applications:

An adhesive composition for coating a tooth cavity on filling and restoring said cavity with a composite resin generally comprising a polymerizable monomer, a filler and a polymerization initiator. In general, this is supplied to dentists as a total system in which said composite resin and this adhesive composition are combined.

A composite resin for filling a tooth cavity. In this case, a filler is incorporated in the adhesive composition of this invention, and the obtained composition is used as a filling material and at the same time has adhesion to teeth.

An adhesive composition for bonding an inlay, onlay, crown or the like to a tooth, or maintaining a bridge, post, split, orthodontic bracket or the like to a tooth, or bonding a crown to an abutment tooth.

Pit and fissure sealant.

When used in the respective applications, the specific composition for the adhesive composition is chosen with reference to the description hereinabove. For example, in a case of the adhesive composition for coating a tooth cavity before filling the composite resin, it may contain 1.5–100% by weight of the aforesaid adhesive vinyl compound in the adhesive composition, diluted with another polymerizable monomer (e.g. Bis-GMA, HEMA, aliphatic dimethacrylate, etc.) or an organic solvent (e.g. ethanol, etc.) and further it may contain room temperature curing type curing agent, in accordance with the recipe shown in U.S. Pat. No. 4,259,075 or U.S. Pat. No. 4,259,117. Where the adhesive composition is used as the composite resin, it is preferred to use that obtained by adding 1.5–50% by weight (based on the total polymerizable monomers) of the aforesaid adhesive vinyl monomer to the conventional filling material consisting of 20–40% by weight of a polymerizable monomer such as Bis-GMA, etc. and 80–20% by weight of a filler. By applying the thus obtained adhesive composition to a tooth in the conventional manner, the cured composite resin strongly adheres to the tooth, and thus the need for any mechanical retention such as an under-cut has been eliminated. [While it is desired to apply the adhesive composition of this invention after acid etching the tooth cavity surface for better adhesive strength, the adhesive composition of this invention can provide practical, satisfactory adhesive strength even without such acid etching as compared with the compositions disclosed in U.S. Pat. Nos. 4,259,075 and 4,259,117, and this is advantageous since there is the risk that acid etching exerts an injurious effect on the pulp]. When an inlay, onlay, crown or the like is to be bonded to a tooth cavity or abutment tooth, it is preferred to use that having a composition of, for example, 1.5–50 parts by weight of an adhesive vinyl monomer, 98.5–50 parts by weight of a copolymerizable monomer and 50–500 parts by weight of a filler. By coating a slight excess of such an adhesive composition on the adherend surface and bringing them into intimate contact, it is now possible to bond them to the tooth. Further, it is now possible to prevent caries by forming a film strongly adhered to the tooth surface by coating a solution containing polymerizable monomers, including an adhesive vinyl monomer, and a polymerization curing agent on the tooth surface and curing it.

(ii) Orthopedic Applications:

The adhesive composition of this invention may be employed as a bone cement for bonding and fixing a ceramic or metal artificial joint or splint to the bone. One preferred example of the composition for the adhesive composition in this case is 90–98.5 parts by weight of methyl methacrylate, 10–1.5 parts by weight of an adhesive vinyl monomer and 50–150 parts by weight of polymethyl methacrylate.

(iii) General industrial and domestic applications:

Since the adhesive composition of this invention has excellent adhesion to metal materials, ceramics and organic polymer materials, it is useful as adhesive for transport machines, electric appliances, building materials, cans and ceramics, as well as for domestic use. Further, it may be used as a paint, a primer for a paint, or a coating agent. When used in such applications, the adhesive composition of this invention has a surprising feature in that it can adhere to the adherend surface not only when it is contaminated with an oil but also with water. Moreover, the adhesive strength is markedly higher than that of any conventional polymerization curing type adhesive, such as cyanoacrylates, epoxy resins, SGA (second generation acrylic adhesives), etc.

Having generally described the invention, a more complete understanding can be obtained by reference to certain specific examples, which are intended for purpose of illustration only and are not intended to be limiting. [Examples of the Production of Adhesive Monomers Used in the Invention]

Production Example 1

36 g of phosphorus oxychloride was dissolved in 100 ml of tetrahydrofuran (THF), placed in a 1-liter flask and cooled to −50° C. 50 g of Bis-GMA and 22 g of triethylamine were dissolved in THF and added dropwise thereto while maintaining the internal temperature of the flask not higher than −40° C. After the addition, the internal temperature was allowed to rise to 0° C., 11 g of water and 49 g of triethylamine dissolved in THF were added dropwise thereto. The reaction mixture was stirred under ice-cold condition for a half day, and the separated triethylamine salt was filtered off. A trace of MEHQ was added to the filtrate, and the solvent was evaporated under reduced pressure to obtain the following phosphate compound:

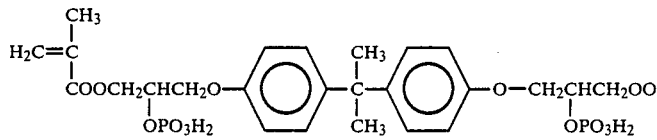

Elementary Analysis:
C=51.3%; H=5.1%; P=9.0%.

Production Example 2

0.3 Mole of methacrylic acid chloride and 0.3 mole of 1,2-aminododecanoic acid were reacted in a mixed solvent of dioxane and water under Schotten Baumann reaction conditions to obtain N-methacryloyl-12-aminododecanoic acid in a yield of 73%.

Then, 30 g of said compound was mixed with 30 g of glycidol and 3 g of triethylbenzylammonium chloride. The mixture was heated to 80° C. to effect the reaction for 4 hours, to obtain the following compound:

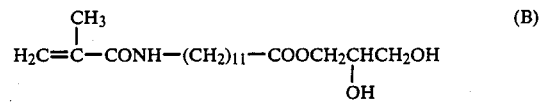

The two hydroxyl groups of said compound (B) were converted to phosphate forms according to the procedures in Production Example 1 to obtain the following compound (C):

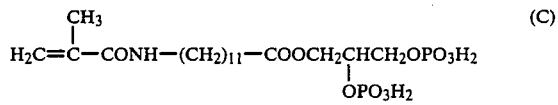

Elementary Analysis:
C=43.6%; H=6.9%; P=11.9%, N=2.1%.

Production Example 3

The N-methacryloyl-12-aminododecanoic acid synthesized in Production Example 2 was reacted with phosphorus pentachloride to synthesize N-methacryloyl-12-aminododecanoyl chloride.

Then, 0.1 mol said acid chloride was reacted with 0.1 mol of 1-hydroxyethane-1,1-diphosphonic acid in DMSO in the presence of 0.3 mol of triethylamine to synthesize the following compound:

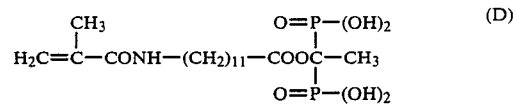

Elementary Analysis:
C=45.2%; H=7.0%; N=2.7%; P=12.8%. [Examples of the Adhesive Composition of this Invention and Use thereof]

EXAMPLE 1

Using the compound (C) synthesized in Production Example 1, a two-pack type primer having the following composition was prepared:

| Formulation I | |
|---|---|
| Bis-GMA | 50 pts. by wt. |
| HEMA | 43 |
| Compound (C) | 7 |
| Benzoyl peroxide | 2 |
| Formulation II | |
| Ethanol | 100 pts. by wt. |
| Sodium benzenesulfinate | 3 |
| N,N—Dimethyl-p-toluidine | 0.7 |

A human molar was imbedded in an epoxy resin in a cylindrical holder, the dental crown was cut off to expose the dentin, and this was used as a specimen for a bonding test. A stainless steel bar of 9 mm in diameter and 25 mm in length was prepared. The dentin surface and one end surface of the stainless steel bar were polished with #1000 abrasive paper, an adhesive backed tape having a hole of 5 mm in diameter was applied to the dentin surface to limit the surface area to be bonded, then equal amounts of Formulation I and Formulation II were mixed and coated thinly on both the dentin surface and the end surface of the stainless steel bar. Immediately thereafter, air was blown onto the coated surfaces to evaporate the ethanol. A commercial dental composite resin (tradename: "Clearfil-F") was kneaded, the obtained paste was mounted on the end surface of the stainless steel stick, and this was pressed against the dentin surface to effect bonding. The specimens were immersed in water at 37° C. thirty minutes after completion of the bonding operation. On the following day, measurement of tensile bond strength was made. Adhesive failure occured at the interface between the dentin and the composite resin, and the adhesive strength was 78 kg/cm².

COMPARATIVE EXAMPLE 1

A test on the bonding to the dentin of human teeth was conducted in the same manner as in Example 1 except that the compound (C) was replaced by a known phosphate compound, that is, 2-methacryloyloxyethyl dihydrogenphosphate to find that its adhesive strength was 13 kg/cm².

EXAMPLE 2

As adherends, round bars (7 mm in diameter and 25 mm in length) made of iron, aluminum, copper, nickel, porcelain, α-alumina, glass, polymethyl methacrylate and polycarbonate were prepared respectively. One end surface of each of these round bars was polished with #1000 abrasive paper to provide each adherend surface. A 5% ethanolic solution of the compound (D) synthesized in Production Example 3 was thinly coated on each adherend surface, and the ethanol was evaporated using an air syringe. Then, equal amounts of the following formulations for preparing a powder - liquid type adhesive composition were mixed, immediately coated on each adherend surface, and the bars of the same kind were bonded together end to end.

| Formulation III | |
|---|---|
| Methyl methacrylate | 100 pts. by wt. |
| Benzoyl peroxide | 1 |
| Formulation IV | |
| Polymethyl methacrylate powder | 100 pts. by wt. |
| Sodium benzenesulfinate powder | 3 |
| N,N—Diethanol-p-toluidine | 1 |

An hour after the bonding, the bonding test specimens were dipped in water and stored at room temperature for 10 days, after which each adhesive strength under tension was measured, to obtain the following results: iron: 460 kg/cm², aluminum: 408 kg/cm², copper: 271 kg/cm², nickel: 418 kg/cm², porcelain: 225 kg/cm², α-alumina: 165 kg/cm², glass: 108 kg/cm², polymethyl methacrylate: 198 kg/cm², and polycarbonate: 142 kg/cm².

COMPARATIVE EXAMPLE 2

The same bonding test as in Example 1 was conducted except that the compound (D) was replaced by 1-methacryloyloxyethane-1,1-diphosphonic acid, to find that the adhesive strength of any of the iron, aluminum, copper, nickel, porcelain, α-alumina and glass was not higher than 50 kg/cm².

EXAMPLE 3

Using the compound (A) synthesized in Production Example 1, a powder - liquid type adhesive composition having the following composition was prepared:

| Formulation V | |
|---|---|
| Bis-GMA | 40 pts. by wt. |
| 2-HEMA | 30 |
| Neopentyl glycol dimethacrylate | 20 |
| Compound (A) | 10 |
| Benzoyl peroxide | 2 |
| MEHQ | trace |
| Formulation VI | |
| Silane-treated quartz powder | 100 pts. by wt. |
| Sodium benzenesulfinate powder | 0.3 |
| N,N—Diethanol-p-toluidine | 0.4 |

The crown part of a bovine anterior tooth was imbedded in an epoxy resin in a cylindrical holder to prepare a bonding test specimen. At that time, the specimen was fixed in the holder with its labial enamel surface exposed in order to enable the bonding to said surface. The labial enamel surface was polished with #1000 abrasive paper, and then acid etched with a 40% orthophosphoric acid aqueous solution for one minute. The acid was washed away with water, and the etched tooth surface was dried by an air syringe, to prepare an adherend surface. Separately, a stainless steel round bar of 7 mm in diameter and 25 mm in length, one end surface of which had been polished with #1000 abrasive paper, was prepared. 0.1 g of Formulation V and 0.3 g of Formulation VI were mixed intimately to prepare a paste adhesive composition, this was coated on said end surface of the stainless steel round bar, and this surface was pressed against the etched tooth surface to effect bonding. An hour after the bonding, the specimen was dipped in water at 37° C., and on the following day, the adhesive strength under tension was measured. Breakage occured at the interface between the enamel and the adhesive composition, and the strength was 171 kg/cm².

EXAMPLE 4

A cylindrical cavity of 4 mm in diameter and 4 mm in depth was formed on the lingual side of a human molar using a diamond bur, and the inside of the cavity was dried using an air syringe. Thereafter, an equal-amount mixed solution of Formulation I and Formulation II employed in Example 1 was coated on the entire surface of the cavity, the ethanol was evaporated by the air syringe, and a commercial dental composite resin (tradename: "Clearfil-F") was filled therein in the conventional manner. After storage in water at 37° C. for a day, this tooth was dipped in dye solution baths at 4° C. and 60° C. 100 times alternately, one minute in each bath, then cut using a cutter, and examined as to whether the dye had penetrated into the bonded interface between the tooth and the filled material. No penetration of the dye was observed.

EXAMPLE 5

A conical cavity of 6 mm in diameter and 4 mm in depth was formed on the occlusal surface of a human molar, and an inlay conforming to the size of this cavity was cast using a Type III gold alloy. Formulation V' in which the compbund (A) incoporated in Formulation V in Example 3 was replaced by the compound (D) was prepared, kneaded with Formulation VI, and the obtained paste was coated on the conical surface of the inlay, which was then pressed into the cavity to effect bonding. Ten minutes after the bonding, this was dipped in water at 37° C., and on the following day, this was subjected to a thermal cycling test comprising dipping in water baths at 4° C. and 60° C. alternately. The inlay still adhered strongly to the tooth even after the thermal cycling test, and when it was tried to peel it off by using the edge of a knife, it was impossible.

EXAMPLE 6

A plate-formed cast 1 mm in thickness and fitting to the lingual surface of a human anterior tooth was prepared using a Ni - Cr alloy (Ni: 76%, Cr: 12%, Mo: 3%, others: 9%). The surface of this cast to be in contact with the tooth was sand blasted with 33μ alumina abrasive grains. On the other hand, the ligual surface of the human anterior tooth was etched with a 40% phosphoric acid aqueous solution for a minute.

Formulation V'' in which the compound (A) incorporated in Formulation V in Example 3 was replaced by the compound (D) was prepared, kneaded with Formulation VI, then coated on the cast surface and pressed against the lingual surface of the human anterior tooth to effect bonding. Ten minutes after the bonding, the tooth was dipped in water at 37° C., and the adhesive strength under tension was measured on the following day, to obtain a value of 160 kg/cm². The adhesive failure occured on the human tooth side.

EXAMPLE 7

A pit and fissure sealant having the following composition was prepared and filled into a fissure of a molar:

| Formulation VII | |
|---|---|
| Bis-GMA | 50 |
| HEMA | 20 |
| Compound (D) | 20 |
| Neopentyl glycol dimethacrylate | 10 |
| Benzoyl peroxide | 1.5 |
| Formulation VIII | |
| Bis-GMA | 50 pts. by wt. |
| HEMA | 30 |
| Neopentyl glycol dimethacrylate | 20 |
| Sodium benzenesulfinate | 2 |
| N,N—Diethanol-p-toluidine | 1.5 |

The fissure of the human molar was cleaned using an explorer, washed with water, dried, and a sealant (an equal amount mixture of Formulations VII and VIII) was filled into the fissure without etching treatment. Ten minutes after the curing, this tooth was dipped in water at 37° C. After storage under the same conditions for a day, this sample was dipped in dye solution baths at 4° C. and 60° C. 100 times alternately, one minute in each bath, cut using a cutter, and examined as to whether the dye had penetrated into the bonded interface between the tooth and the filled material. No penetration of the dye was observed.

EXAMPLE 8

A cylindrical cavity of 4 mm in diameter and 4 mm in depth was formed on the buccal surface of a human tooth using a diamond bur, then the cavity wall was acid etched with a 40% phosphoric acid aqueous solution for a minute, washed with water, and dried. Thereafter, a paste obtained by mixing Formulations VI and V for the powder - liquid type adhesive composition in Example 3 in a ratio by weight of 3:1 was filled into this cavity. Ten minutes after the curing, the sample was dipped in water at 37° C., and when the degree of the dye penetration into the bonded intersurface was examined according to the method in Example 4, the penetration was hardly observed.

What is claimed is:

1. An adhesive composition which comprises 1 part by weight of (a) a compound of the general formula:

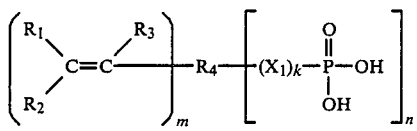

wherein $R_1$ represents H, a hydrocarbon group of 1–6 carbon atoms, a hydrocarbon group of 1–6 carbon atoms containing halogen, COOR', wherein R' represents a hydrocarbon group of 1–20 carbon atoms, a hydrocarbon group of 1–20 carbon atoms containing halogen or halogen;

$R_2$ is as defined for $R_1$;

$R_3$ represents H, a hydrocarbon group of 1–6 carbon atoms, a hydrocarbon group of 1–6 carbon atoms containing halogen, halogen or CN;

$H_4$ represents $(COX_2)_{m1}(CO)_{m2}(ZCO)_{m3}(Z)_{m4}Ra$ wherein Ra represents an organic residue of 6–60 carbon atoms and a valency of m+n; m1, m2, m3 and m4 each represents an integer of 0–4 and satisfies $m1+m2+m3+m4 \leq m$; $X_2$ represents O, S or NRb, wherein Rb represents H or alkyl of 1–4 carbon atoms and Z represents O or S;

$X_1$ is as defined for $X_2$;

m is an integer of 1–4;

n is an integer of 2–6; and k is 0 or 1, and 0–199 parts by weight of (b) a vinyl monomer copolymerizable with the aforesaid compound.

2. The adhesive composition according to claim 1 wherein the aforesaid compound (a) is a vinyl compound of the general formula:

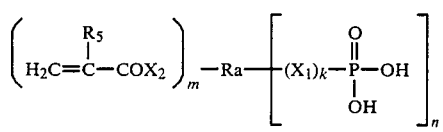

wherein $R_5$ represents hydrogen or methyl, and Ra, $X_1$, $X_2$, k, m and n are as defined in claim 1.

3. The adhesive composition according to claim 2 wherein n is 2.

4. The adhesive composition according to claim 3 wherein the aforesaid vinyl compound is a compound of the general formula:

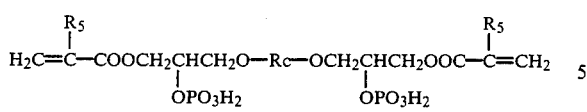

wherein $R_5$ represents hydrogen or methyl, and $R_c$ represents a divalent organic residue of 2-54 carbon atoms.

5. The adhesive composition according to claim 3 wherein the aforesaid vinyl compound is a compound of the general formula:

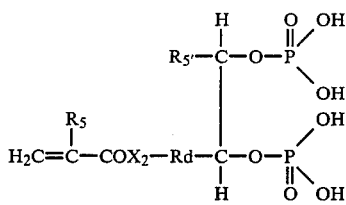

wherein $R_5$ and $R_5'$ each represents hydrogen or methyl, $X_2$ is as defined in claim 1, and $R_d$ represents a divalent organic residue of 4-57 carbon atoms.

6. The adhesive composition according to claim 3 wherein the aforesaid vinyl compound is a compound of the general formula:

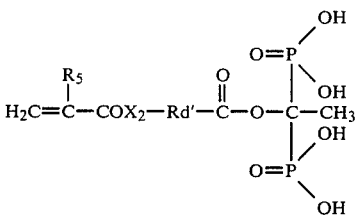

wherein $R_5$ represents hydrogen or methyl, $X_2$ is as defined in claim 1, and $R_d'$ represents a divalent organic residue of 3-57 carbon atoms.

7. The adhesive composition according to claim 1 which further contains 0.01-20 parts by weight of a curing agent per 100 parts by weight of the aforesaid polymerizable monomers.

8. The adhesive composition according to claim 1 which further contains a volatile organic solvent having a boiling point of 150° C. or below at 760 Torr in an amount in the range of up to 300 times by weight that of said polymerizable monomers.

9. The adhesive composition according to claim 1 which further contains 20-500 parts by weight of a filler per 100 parts by weight of said polymerizable monomers.

10. The adhesive composition according to claim 1 wherein said vinyl monomer (b) is a (meth)acrylate type monomer, a styrene type monomer or vinyl acetate.

11. The adhesive composition according to claim 7 wherein said curing agent is a redox type polymerization initiator.

12. The adhesive composition according to claim 7 wherein said curing agent is a photosensitizer.

* * * * *